United States Patent [19]
Krespan

[11] 3,962,325
[45] June 8, 1976

[54] TRIFLUOROMETHYLMALONYL FLUORIDE

[75] Inventor: Carl George Krespan, Wilmington, Del.

[73] Assignee: E. I. Du Pont de Nemours and Company, Wilmington, Del.

[22] Filed: Oct. 4, 1973

[21] Appl. No.: 403,416

[52] U.S. Cl. .......................... 260/544 F; 260/257; 260/585.5; 424/254
[51] Int. Cl.² ......................................... C07C 55/08
[58] Field of Search ................................ 260/544 F

[56] References Cited
UNITED STATES PATENTS

| | | | |
|---|---|---|---|
| 3,647,887 | 3/1972 | Anello et al. | 260/544 F |
| 3,700,733 | 10/1972 | Sweeney et al. | 260/544 F |
| 3,733,357 | 5/1973 | England | 260/544 F |

*Primary Examiner*—Norman Morgenstern

[57] ABSTRACT

Trifluoromethyl compounds of the formulas

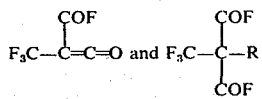

are useful as oil repellants. Substituted barbituric acid derivatives thereof of the formula

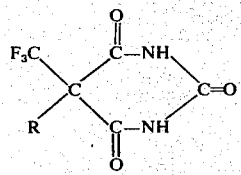

are useful as central nervous system depressants for animals. Trifluoromethylfluorocarbonylketene and trifluoromethylmalonyl fluoride are prepared by reacting perfluoromethylacryloyl fluoride with a carboxylic acid.

1 Claim, No Drawings

TRIFLUOROMETHYLMALONYL FLUORIDE

BACKGROUND OF THE INVENTION

1. Field of the Invention

This invention is concerned with a new class of fluorinated organic compounds and methods for their preparation.

2. Description of the Prior Art

U.S. Pat. No. 3,733,357 discloses the perfluoromalonyl fluorides, $(CF_3)_2C(COF)_2$ and $CF_3CF(COF)_2$, which are useful as water repellants. The copending application of D. C. England, Ser. No. 267,126, filed June 28, 1972 discloses perfluoromethylpropionylketene, $CF_3C(=C=O)COCF_2CF_3$, which is also useful as a waterproofing agent.

C. E. Inman et al. in U.S. Pat. No. 3,141,040 teach 5-ethyl-5-fluorobarbituric acid,

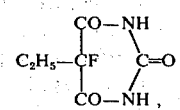

and R. deV. Huber et al. in U.S. Pat. No. 2,721,201 teach 5-alkyl (or allyl)-5-monofluoroalkylbarbituric acids,

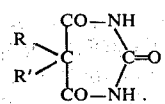

SUMMARY OF THE INVENTION

It has now been discovered that trifluoromethyl compounds of the formula

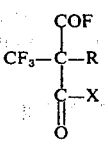

in which R is hydrogen or hydrocarbyl of up to 8 carbon atoms selected from the group consisting of alkyl, alkenyl and aralkyl, and X is F, with the proviso that R and X may be taken together to form a second bond between the carbon atoms to which they are attached, are useful as oil repellants. These compounds are trifluoromethylfluorocarbonylketene of the formula

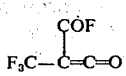

and trifluoromethyldicarbonyl fluoride compounds of the formula

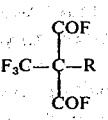

It has also been discovered that trifluoromethylfluorocarbonylketene and trifluoromethylmalonyl fluoride can be prepared by a novel process which comprises reacting perfluoromethylacryloyl fluoride with a carboxylic acid of the formula R'COOH wherein R' is hydrocarbyl of up to 17 carbon atoms in a mole ratio of from about 1:100 to 100:1. It has also been discovered that trifluoromethyl barbituric acids of the formula

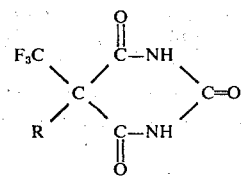

wherein R is hydrocarbyl of up to 8 carbon atoms selected from the group consisting of alkyl, alkenyl and aralkyl, which are derived from the trifluoromethyldicarbonyl fluorides of this invention, are useful as central nervous system depressants for animals.

DETAILED DESCRIPTION OF THE INVENTION

The present invention may be illustrated by the following reactions:

$R'COOH + CF_2=C(CF_3)COF \rightarrow$

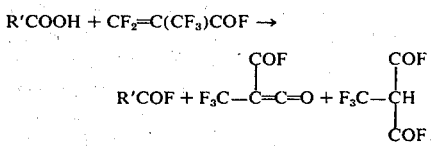

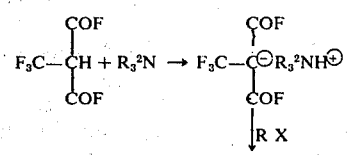

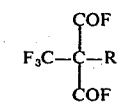

$\downarrow RX$

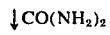

$\downarrow CO(NH_2)_2$

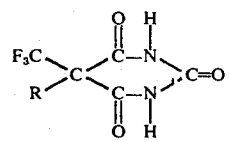

in which R' is hydrocarbyl of up to 17 carbon atoms, the $R^2$ groups, alike or different, are alkyl groups of up to 8 carbon atoms, phenyl, benzyl, or two or three of them taken together with the nitrogen may form a 5- or 6-membered heterocyclic ring compound. The compound $R^2_3N$ is a salt-forming tertiary amine. R is hydrocarbyl of 8 carbon atoms selected from the group consisting of alkyl, alkenyl, alkenyl, aralkyl, and the compound RX is an alkylating, alkenylating or aralkylating agent. Thus, X may be alkyl sulfate, fluorosulfate, benzenesulfonyloxy, trifluoromethylsulfonyloxy, and the like. When R is alkenyl, X may also be halogen as in chloro, bromo and iodo.

The reaction of perfluoromethacryloyl fluoride with a carboxylic acid to form trifluoromethylmalonyl fluoride, trifluoromethylfluorocarbonylketene, and an acid fluoride is exothermic and may be carried out in the temperature range from about 0° to 150°C. At temperatures below 60°C, the reaction appears to take place in two steps with the first formation of an adduct of the two reactants which adduct must be heated above 60°C to initiate formation of the final products. Pressure is not a critical factor in the reaction and pressures both above and below atmospheric pressure may be used. Atmospheric pressure is preferred for convenience. The time for the reaction to take place varies from about 1–2 minutes to several hours, depending on the temperature employed. The reaction may be carried out neat. Optionally, solvents which are inert to the reactants and products may be employed. Suitable solvents include halogenated hydrocarbons such as $CCl_4$ and aromatic hydrocarbons such as benzene and toluene.

The molar proportions in which perfluoromethacryloyl fluoride and the carboxylic acid are brought together to accomplish this reaction may be varied widely, e.g., from about 1:100 to about 100:1, since under all these conditions at least some of each of the three products will be formed. For practical yields, it is preferred to employ molar ratios within the range from about 2:1 to 0.9:1. The acids of the formula R'COOH which are suitable for use in this process are those in which R' is hydrocarbyl of up to 17 carbon atoms. Suitable acids include acetic, propionic, butyric, isovaleric, hexanoic, octanoic, nonanoic, benzoic, dodecanoic, lauric, palmitic, oleic, stearic, and the like. The preferred acids are those in which R' is alkyl of up to 8 carbon atoms.

The reaction of perfluoromethacryloyl fluoride with the carboxylic acid may be carried out either with or without the addition of $P_2O_5$. Under some circumstances, the addition of $P_2O_5$ appears to increase the proportion of trifluoromethylfluorocarbonylketene in the product.

The hydrogen atom in trifluoromethylmalonyl fluoride is active and permits ready alkylation of the compound to yield alkyl-, alkenyl-, and aralkyl-trifluoromethylmalonyl fluorides. This is in high contrast to perfluoromethylmalonyl fluoride, which is substantially inert to common alkylating reactions. Alkylation of trifluoromethylmalonyl fluoride is readily accomplished by treating its tertiary amine salt with an alkylating agent. A wide variety of tertiary amines, as defined above, may be used in forming the salt. Trimethylamine, triethylamine, and pyridine are representative examples. The alkylating agent R X is preferably a known active alkylating agent such as where X is alkyl sulfate, fluorosulfate, or trifluoromethylsulfonyl. Where R is allylic, X may be less active such as Cl.

The alkylation may be carried out neat but is preferably conducted in the presence of a solvent which is inert to the reactants and products. Suitable solvents include diethyl ether, methylene chloride, and benzene. Alkylations of the type described may be carried out over a wide range of temperatures but are preferably conducted in the range of about 25°–90°C. The reaction should be allowed to proceed from about 1–2 hours to several days to obtain a maximum yield.

Substituted barbituric acids may be prepared from the alkylated trifluoromethylmalonyl fluoride. The reaction of the alkyl-, alkenyl- or aralkyl-trifluoromethylmalonyl fluoride with urea is carried out in the presence of pyridine and a solvent in a manner analogous to known syntheses of barbituric acid derivatives from urea and other derivatives of malonic acid.

Tertiary amines of the formula $R^2_3N$ operable in the salt-forming reaction include trimethylamine, triethylamine, tributylamine, N,N-dimethyloctylamine, N,N-diethylaniline, triphenylamine, tribenzylamine, pyridine, N-methylpiperidine, N-ethylpyrrole, N-methylpyrrolidine, and the like.

Alkylating agents suitable for reaction with the tertiary amine salts of trifluoromethylmalonyl fluoride include dimethyl sulfate, diethyl sulfate, ethyl fluorosulfate, n-butyl trifluoromethanesulfonate, isopropyl benzenesulfonate, allyl bromide, crotyl chloride, and benzyl bromide.

Trifluoromethylfluorocarbonylketene may be obtained free of trifluoromethylmalonyl fluoride by two alternate procedures. In the first of these, perfluoromethacryloyl fluoride is condensed with methanol and the condensate hydrolyzed to obtain 3,3-difluoro-3-methoxy-2-trifluoromethylpropionic acid which when heated with $P_2O_5$ yields trifluoromethylfluorocarbonylketene. This process is illustrated in Example 4. In the second procedure, trifluoromethylmalonyl fluoride is dehydrofluorinated by the action of $SO_3$ to yield a mixture of trifluoromethylfluorocarbonylketene and pyrosulfuryl fluoride. The mixture is readily separated into its components by distillation as shown in Example 5.

The utility of compounds of the formulas $CF_3C(=C=O)COF$ and $CF_3CR(COF)_2$ for imparting oil repellency to cellulosic materials is shown in Examples 14 and 15. The utility of the substituted barbituric acids as central system depressants for rodents is shown in Example 16.

EXAMPLES OF THE INVENTION

The following Examples, illustrating the novel products and process of this invention, are given without any intention that the invention be limited thereto. All parts and percentages are by weight unless otherwise specified.

EXAMPLE 1

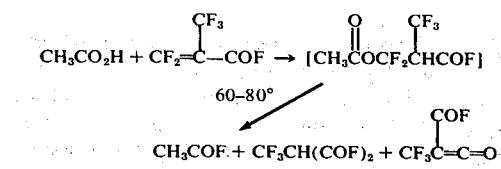

Dropwise addition of 6.6 g (0.11 mol) of acetic acid to 19 g (0.11 mol) of perfluoromethacryloyl fluoride resulted in an exothermic reaction, and cooling was applied to keep the temperature below 50°C. When the addition was complete, the mixture was cooled to 25°C, stirred for 30 minutes, and then heated to 60°C. The volatile product driven off by heating was 4.5 ml of acetyl fluoride, identified by infrared (ir) absorption analysis. The remaining liquid was added to 15.9 g (0.11 mol) of $P_2O_5$ and distilled to yield 14.1 g of distillate boiling at 55°–60.5°C. Nuclear magnetic resonance (nmr) analysis of one of the later fractions showed it to be a 2:1 mixture of trifluoromethylmalonyl fluoride and trifluoromethylfluorocarbonylketene. Bands attributable to the malonyl fluoride (5.38 and 5.42 $\mu$ for COF) as well as the ketene were shown by ir. Further treatment of a portion of the mixture with $P_2O_5$ did not increase the proportion of ketene.

EXAMPLE 2

The first reaction of Example 1 was repeated and the acetyl fluoride, bp 20°–25°C, removed by heating the adduct above 70°C. Distillation of the remainder gave 15.1 g of distillate with bp 58°–64°C (78% yield calculated as $CF_3CH(COF)_2$). $^{19}F$ nmr analysis of this product indicated a 17:1 mixture of trifluoromethylmalonyl fluoride and trifluoromethylfluorocarbonylketene; ir (CCl$_4$): 3.38 $\mu$ (CH), 5.38 and 5.42 $\mu$ (C=O) for $CF_3CH(COF)_2$ with weak bands at 4.57 (C=C=O) and 5.47 $\mu$ (shoulder C=O) for $CF_3C(=C=O)COF$; nmr (CCl$_4$): $^{19}F$ at 46.4 (quartet, $J_{FF} = 10$ Hz, 2, CO$\underline{F}$) and −66.0 ppm (triplet, $J_{FF} = 10$ Hz, into doublets, $J_{HF} = 7$ Hz, 3, C$\underline{F}_3$) with previously assigned peaks for $CF_3C(=C=O)COF$ also present in 5.5 % amount.

Anal. Calcd for $C_4HF_5O_2$: C, 27.29; H, 0.57; F, 53.96. Found: C, 27.75; H, 0.79; F, 54.34.

Pure trifluoromethylmalonyl fluoride can be separated from its mixture with a minor proportion of trifluoromethylfluorocarbonylketene by careful fractional distillation, first fractionating off a mixture of the two compounds and then distilling pure trifluoromethylmalonyl fluoride from the mixture.

EXAMPLE 3

Reaction of 178 g (1.00 mol) of perfluoromethacryloyl fluoride and 61.2 g (1.02 mol) of acetic acid was carried out at 30°–40°C. The reaction mixture was heated at 80°–85°C to eliminate acetyl fluoride (bp 20°–22°C), and the product distilled at bp 60°–63°C to give 162.1 g (92%). Infrared analysis indicated about 5% of $CF_3C(=C=O)COF$ in $CF_3CH(COF)_2$.

EXAMPLE 4

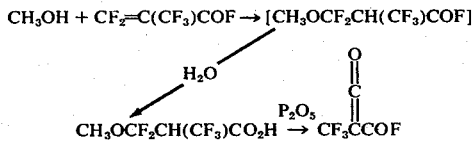

Part A

A solution of 50 g (0.28 mol) of perfluoromethacryloyl fluoride in 100 ml of ether was stirred at 0°C while 9.0 g (0.28 mol) of methanol was added at a rate sufficient to keep the reaction mixture near 20°C. When the addition was complete, 100 g of anhydrous NaF was added, and the mixture was stirred while 5.4 g (0.30 mol) of water was added. The temperature was not allowed to go above 35°C. After having stood overnight, the reaction mixture was filtered and distilled. It was necessary to keep the pot temperature below 70°C to avoid excessive etching. 3,3-Difluoro-3-methoxy-2-trifluoromethylpropionic acid was obtained as 22.1 g (38%) of distillate, bp 45°C (0.5 mm); ir (neat): 3.25 (broad, OH), 5.72 (C=O), 7.5-9 $\mu$ (CF, COC); nmr (CCl$_4$): $^1H$ at 11.8 (singlet, 1, O$\underline{H}$), 3.83 (sextet (quartet, $J_{HF} = 7.5$ Hz, into triplets, $J_{HF} = 7.5$ Hz), 1, C$\underline{H}$), and 3.67 ppm (singlet, 3, OCH$_3$); $^{19}F$ at −65.1 ppm (triplet, $J_{FF} = 10.5$ Hz, into doublets, $J_{HF} = 7.5$ Hz, 3, C$\underline{F}_3$) and 14 lines from overlapping center lines of an AB pattern at −4233 Hz and −4247 Hz (both quartets, $J_{FF} = 10.5$ Hz, into doublets, $J_{HF} = 7.5$ Hz, 2, C$\underline{F}_2$).

Anal. Calcd for $C_5H_5F_5O_3$: C, 28.86; H, 2.42. Found: C, 29.30; H, 2.57.

Part B

A mixture of 7.2 g (0.035 mol) of 3,3-difluoro-3-methoxy-2-trifluoromethylpropionic acid and 45 g of $P_2O_5$ was heated at 120°–160°C and product was distilled directly from the reaction mass. There was thus obtained 0.93 g (17%) of trifluoromethylfluorocarbonylketene, bp 58°C; ir (CCl$_4$): 4.56 (C=C=O), 5.47 (COF), and 7.2-8.5 $\mu$ (CF); nmr (CCl$_4$): $^{19}F$ at 33.3 (quartet, $J_{FF} = 11.5$ Hz, 1, CO$\underline{F}$) and −56.0 ppm (doublet, $J_{FF} = 11.5$ Hz, 3, C$\underline{F}_3$). Mass spec: m/e 156 (M$^+$) 137 (M$^+$-F), and 128 (M$^+$-CO).

Anal. Calcd for $C_4F_4O_2$: C, 30.79; F, 48.71. Found: C, 29.49; F, 47.86.

EXAMPLES 5

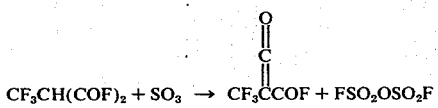

A mixture of 17.6 g (0.10 mol) of trifluoromethylmalonyl fluoride (containing ca. 5% of the ketene) and 24 g (0.3 mol) of $SO_3$ was heated and crude distillate was redistilled to provide 11.9 g (40%) of pyrosulfuryl fluoride, bp 51°–54°C, and 2.4 g (15%) of trifluoromethylfluorocarbonylketene, bp 58°–59.5°C. Pyrosulfuryl fluoride was identified by comparison of bp, infrared spectrum and nmr spectrum with those reported for authentic samples. The ketene was shown in infrared to be the same as that prepared in Example 4.

Anal. Calcd for $C_4F_4O_2$: C, 30.79; F, 48.71. Found: C, 29.95; F, 48.50.

EXAMPLE 6

This example illustrates the separation of trifluoromethylfluorocarbonylketene from its mixture with trifluoromethylmalonyl fluoride by heating it with ketene. To 20 ml of trifluoromethylmalonyl fluoride containing about 5% of trifluoromethylfluorocarbonylketene was added 10 ml of ketene (measured at −80°C) by passing the mixture and the ketene simultaneously at atmospheric pressure through a "Pyrex" tube heated at 200°C, the passage being spread uniformly over a 15-minute period. The product, collected in a condenser at −80°C, was transferred at 5 mm to another cold trap and then warmed to 25°C to give 13 ml (65% recovery) of trifluoromethylmalonyl fluoride which was shown by ir to be free of trifluoromethylfluorocarbonylketene.

EXAMPLE 7

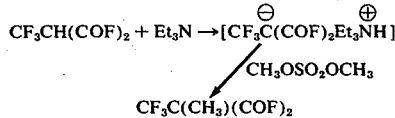

A solution of 17.6 g (0.10 mol) of $CF_3CH(COF)_2$ in 25 ml of ether was cooled at 0°C and stirred while 9.2 g (0.10 mol) of triethylamine was added dropwise in 15 minutes. Then 25.2 g (0.20 mol) of dimethyl sulfate was added all at once, and the mixture was allowed to stand at 25°C for 3 hours. Distillation gave 9.3 g (49%)

of methyltrifluoromethylmalonyl fluoride, bp 62°–65°C. Redistillation gave an analytical sample, bp 64°–65.5°C; ir and nmr spectra were taken on a similarly prepared sample; ir (CCl$_4$): 5.37 (COF) and 7.5–8.5 $\mu$ (CF); nmr (CCl$_4$): $^1$H at 1.92 ppm (broadened singlet, C$\underline{H}$$_3$); $^{19}$F at 37.8 (quartet, J$_{FF}$ = 10 Hz into quartets, J$_{HF}$ = 1 Hz, 2, (CO$\underline{F}$) and −71.1 ppm (triplet, J$_{FF}$ = 10 Hz, into quartets, J$_{HF}$ = 0.8 Hz, 3, C$\underline{F}$$_3$).

Anal. Calcd for C$_5$H$_3$F$_5$O$_2$: C, 31.60; H, 1.59; F, 49.98. Found: C, 31.83; H, 1.49; F, 50.31.

EXAMPLE 8

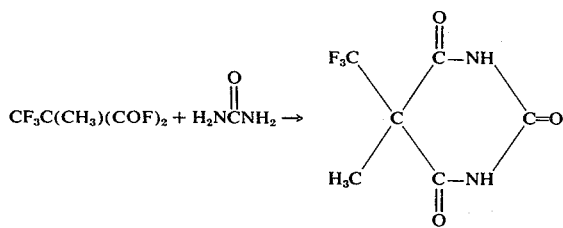

CF$_3$C(CH$_3$)(COF)$_2$ + H$_2$NCNH$_2$ →

To a suspension of 1.50 g (0.025 mol) of urea in 30 ml of glyme and 4.0 g (0.050 mol) of pyridine was added dropwise with stirring a solution of 5.0 g (0.026 mol) of methyltrifluoromethylmalonyl fluoride in 20 ml of glyme. Urea dissolved during a mildly exothermic reaction and the homogeneous solution was allowed to stand overnight. The mixture was then refluxed briefly, solvent was removed under vacuum, and the residue was stirred with 25 ml of water. Filtration and rinsing with water gave 3.80 g of 5-methyl-5-trifluoromethylbarbituric acid, mp 205°–206.5°C. A second crop, mp 205°–207°C, 0.84 g, brought the yield to 88% (4.64 g). Recrystallization from water gave an analytical sample, mp 205°–206°C; ir (KBr): 3.07 and 3.17 (NH), 5.67 shoulder and 5.80 (C=O), and 8–8.5 $\mu$ (CF); nmr ((CD$_3$)$_2$CO): $^1$H at ca. 7.0 (very broad, 2 (partly exchanged into acetone-d$_6$), N$\underline{H}$) and 1.72 ppm (quartet, J$_{HF}$ = 0.7 Hz, 3, C$\underline{H}$$_3$); $^{19}$F at −70.8 ppm (quartet, J$_{HF}$ = 0.7 Hz, C$\underline{F}$$_3$).

Anal. Calcd for C$_6$H$_5$F$_3$N$_2$O$_3$: C, 34.30; H, 2.40; F, 27.13; N, 13.33. Found: C, 34.44; H, 2.56; F, 27.31; N, 13.34.

EXAMPLE 9

Part A

Addition of 14.1 g (0.14 mol) of triethylamine to a solution of 25.2 g (0.14 mol) of trifluoromethylmalonyl fluoride in 25 ml of ether was carried out at 0°C with stirring. To the resulting homogeneous solution was added 30.8 g (0.20 mol) of diethyl sulfate and the mixture was then allowed to warm to 25°C. Distillation provided 8.3 g of liquid with bp ca. 45°C (230 mm). Redistillation gave 5.2 g (18%) of ethyltrifluoromethylamalonyl fluoride, bp 84°–85.5°C; ir (CCl$_4$): 3.38 and 3.45 (satd. CH), 5.39 (COF), and 7.5–8.5 $\mu$ (CF); nmr (CCl$_4$): $^1$H at 2.43 (quartet, J$_{HH}$ = 7.5 Hz, 2, C$\underline{H}$$_2$) and 1.23 ppm (triplet, J$_{HH}$ = 7.5 Hz, 3, C$\underline{H}$$_3$; $^{19}$F at 40.6 (quartet, J$_{FF}$ = 10 Hz, 2, CO$\underline{F}$) and −67.8 ppm (triplet, J$_{FF}$ = 10 Hz, 3, C$\underline{F}$$_3$).

Anal. Calcd for C$_6$H$_5$F$_5$O$_2$: C, 35.31; H, 2.47; F, 46.54. Found: C, 35.45; H, 2.37; F, 46.26.

Part B

When methylene chloride was substituted for ether in the above procedure, the yield of ethyltrifluoromethylmalonyl fluoride was 15%.

EXAMPLE 10

A solution of 9.2 g (0.09 mol) of triethylamine in 25 ml of ether was added dropwise to a stirred solution of 17.6 g (0.10 mol) of trifluoromethylmalonyl fluoride in 50 ml of ether at −80°C. To the resulting suspension of solid was added 14.1 g (0.11 mol) of ethyl fluorosulfate and the mixture was then allowed to warm to 25°C with stirring. The homogeneous reaction mixture developed two layers after standing overnight. Distillation gave 15 g (74%) of ethyltrifluoromethylmalonyl fluoride, bp 54°–56°C (260 mm), identified by ir.

EXAMPLE 11

A mixture of 1.70 g (0.028 mol) of urea, 4.4 g (0.056 mol) of pyridine and 30 ml of glyme was stirred at 25°C while a solution of 5.7 g (0.028 mol) of ethyltrifluoromethylmalonyl fluoride in 20 ml of glyme was added rapidly. The mixture was stirred overnight, solvent was removed under vacuum, and the residue was stirred with 15 ml of water. Filtration provided a solid which was recrystallized from water to give 3.8 g of 5-ethyl-5-trifluoromethylbarbituric acid, mp 210°–211°C. A second crop, 0.2 g, mp 208°–209°C, raised the total to 4.0 g (64%). A sample was recrystallized twice from water for analysis, mp 211°C; ir (KBr): 3.05 and 3.18 (NH), 3.49 (satd. CH), 5.72 and 5.82 (C=O), and 8–8.5 $\mu$ (CF); nmr ((CD$_3$)$_2$CO): $^1$H at ca. 8.5 (very broad (partly exchanged into acetone-d$_6$), 2, N$\underline{H}$), 2.37 (quartet with fine structure, J$_{HH}$ = 7.5 Hz, 2, C$\underline{H}$$_2$); and 0.94 ppm (triplet, J$_{HH}$ = 7.5 Hz, 3, C$\underline{H}$$_3$); $^{19}$F at −69.3 ppm (singlet with fine structure, C$\underline{F}$$_3$).

Anal. calcd for C$_7$H$_7$F$_3$N$_2$O$_3$: C, 37.51; H, 3.15; F, 25.43; N, 12.50. Found: C, 37.41; H, 3.19; F, 25.60; N, 12.53.

EXAMPLE 12

To 17.6 g (0.10 mol) of trifluoromethylmalonyl fluoride and 50 ml of ether stirred at −80°C was added dropwise a solution of 9.2 g (0.09 mol) of triethylamine in 25 ml of ether. Then 12.5 g (0.12 mol) of 1-chloro-3-methyl-2-butene was added, and the mixture was stirred at 25°C until homogeneous. After standing at 25°C for 3 days, the mixture was distilled to give 3.9 g (16%) of (3-methyl-2-butenyl)-trifluoromethylmalonyl fluoride, bp 43°–45°C (20 mm); ir (CCl$_4$): 3.31, 3.37 and 3.42 (CH), 5.36 (C=O) and 7.5–8.5 $\mu$ (CF).

EXAMPLE 13

A mixture of 0.96 g (0.016 mol) of urea, 2.45 g (0.031 mol) of pyridine and 20 ml of glyme was stirred at 25°C while 3.8 g (0.0155 mol) of (3-methyl-2-butenyl)trifluoromethylmalonyl fluoride in 10 ml of glyme was added rapidly. The mixture was stirred overnight, heated for 10 minutes at 70°C, and evaporated to a viscous residue. Trituration of the residue with 20 ml of water gave 2.7 g (66%) of 5-(3-methyl-2-butenyl)-5-trifluoromethylbarbituric acid, mp 150°–153°C. A sample for analysis was recrystallized from water, mp 154°–155°C; ir (KBr): 3.04 and 3.18 (N$\underline{H}$), 3.32, 3.39 and 3.44 (CH), 5.63 and 5.81 (C=O), and 8–8.5 $\mu$ (CF). Raman ir spectrum showed C=C at 5.95 $\mu$; nmr ((CD$_3$)$_2$CO): $^1$H at ca. 9.0 (very broad (partly exchanged into acetone-d$_6$), 2, N$\underline{H}$), 5.03 (triplet, J$_{HH}$ = 7.7 Hz, 1, =C$\underline{H}$), 3.07 (doublet, J$_{HH}$ = 7.7 Hz, 2, =CC$\underline{H}_2$), 1.69 and 1.67 ppm (singlets, 6, =CC$\underline{H}_3$); $^{19}$F at −69.0 ppm (singlet, C$\underline{F}_3$).

Anal. Calcd for C$_{10}$H$_{11}$F$_3$N$_2$O$_3$: C, 45.46; H, 4.20; F, 21.57; N, 10.60. Found: C, 45.78; H, 4.27; F, 21.84; N, 10.43.

EXAMPLE 14

Trifluoromethylmalonyl fluoride, trifluoromethylfluorocarbonylketene and the substituted trifluoromethylmalonyl fluorides are useful for imparting oil repellency to cellulosic materials. This was shown as follows. Circles of cellulosic filter paper (Whatman 5) were thoroughly moistened, respectively, with (a) a 20:1 mixture of trifluoromethylmalonyl fluoride and trifluoromethylfluorocarbonylketene, and (b) ethyltrifluoromethylmalonyl fluoride, and dried in air until there was no visible difference between the treated papers and an untreated control. Three papers, one treated with (a), one with (b) and one control were placed on a flat surface. In the center of each paper two drops of refined heavy mineral oil ("Nujol") were placed together. At selected intervals from the time of placing the oil, the visible diameters of the oil spots on the papers were measured as follows:

Diameter of Oil Spot (mm)

| Time from Start (min) | CF$_3$CH(COF)$_2$/ CF$_3$C(=C=O)COF | CF$_3$C- (C$_2$H$_5$)- (COF)$_2$ | Untreated Control |
| --- | --- | --- | --- |
| 2 | 9 | 8 | 15 |
| 5 | 10 | 10 | 19 |
| 10 | 11 | 11 | 22 |
| 20 | 14 | 13 | 27 |

At the end of the test the oil drops on the treated papers remained as beads above the surface of the paper, whereas in the untreated control the drop had been absorbed into the paper.

EXAMPLE 15

Filter papers treated with the compounds of this invention were prepared as in Example 14. Oil emulsions prepared by vigorous shaking of 0.5 ml of "SAE-10-30" motor oil in 50 ml of distilled water were then filtered by gravity through the treated papers and an untreated control. The filtrate through the paper treated with (a) was clear and had only a trace of oil on the surface. The filtrate through the paper treated with (b) was clear and showed no trace of oil on the surface. The filtrate through the untreated paper was turbid and there was a visible layer of separated oil on the surface.

EXAMPLE 16

The substituted barbituric acids of this invention are useful as central nervous system depressants for rodents. This has been demonstrated in white mice as follows. The compounds were administered orally to groups of test animals and the minimum dosage was determined which was effective in causing 50% of the test animals to show evidence of ataxia or of failure in the vertical bar test (ED/50). The test for ataxia involved visual observation of any deviation, lack of coordination or failure in the gait of the test animal as it walked across a flat surface. In the vertical bar test, the animal was placed upside down at the upper end of a 12 inch vertical bar five-eighth inch in diameter which was covered with cloth tape to facilitate grip. A control animal will grasp the bar, climb down the bar first and dismount. The test compound was considered active if there was any failure of the test animal to grasp the bar or to climb down and dismount in a coordinated manner.

the The barbituric acids of Examples 8, 11 and 13 were tested as described above and the minimum effective dosages (ED/50) in the two tests were as follows. Dosage numbers shown are in mg of the test compound per kg of body weight of the test animal.

| Product Of Example | Barbituric Acid Derivative | Ataxia Test (ED/50) | Vertical Bar Test (ED/50) |
| --- | --- | --- | --- |
| 8 | 5-Methyl-5-trifluoromethylbarbituric acid | 200 | 100 |
| 11 | 5-Ethyl-5-trifluoromethylbarbituric acid | 20 | 36 |
| 13 | 5-(3-Methyl-2-butenyl)-5-trifluoromethylbarbituric acid | 60 | 60 |

Although the invention has been described and exemplified by way of specific embodiments, it is not intended that it be limited thereto. As will be apparent to those skilled in the art, numerous modifications and variations of these embodiments can be made without departing from the spirit of the invention or the scope of the following claims.

I claim:

1. Trifluoromethylmalonyl fluoride of the formula

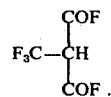

* * * * *